United States Patent [19]

Onodera et al.

[11] Patent Number: 4,902,843
[45] Date of Patent: Feb. 20, 1990

[54] PROCESS FOR PRODUCING M-XYLENE FROM O-XYLENE

[75] Inventors: Tamio Onodera; Akio Namatame, both of Matsuyama, Japan

[73] Assignee: Teijin Petrochemical Industries, Ltd., Tokyo, Japan

[21] Appl. No.: 253,215

[22] Filed: Oct. 4, 1988

[30] Foreign Application Priority Data

Oct. 5, 1987 [JP] Japan .............................. 62-249916

[51] Int. Cl.$^4$ ................................................ C07C 5/22
[52] U.S. Cl. ..................................... 585/481; 585/828
[58] Field of Search ................................. 585/481, 828

[56] References Cited

U.S. PATENT DOCUMENTS

| | | | |
|---|---|---|---|
| 3,558,732 | 1/1971 | Neuzil | 585/828 |
| 3,578,723 | 5/1971 | Bowes et al. | 585/481 |
| 3,766,287 | 7/1971 | Stenmark et al. | 585/481 |
| 3,813,452 | 5/1974 | Bieser | 525/828 |
| 3,907,914 | 9/1975 | Willis, Jr. et al. | 585/481 |
| 3,939,221 | 2/1976 | Pearce | 585/828 |
| 4,554,146 | 11/1985 | Vaughan | 423/118 |
| 4,697,039 | 9/1987 | Schmidt | 585/481 |

*Primary Examiner*—Patrick P. Garvin
*Assistant Examiner*—E. D. Irzinski
*Attorney, Agent, or Firm*—Wenderoth, Lind & Ponack

[57] ABSTRACT

A process for producing m-xylene, which comprises isomerizing a hydrocarbon material containing o-xylene as a main ingredient in the presence of a catalyst composition comprising zeolite ZSM-4 and/or zeolite omega under such conditions that m-xylene is selectively formed, and recovering m-xylene by distillation from the resulting isomerization mixture containing o-xylene and m-xylene as main ingredients.

10 Claims, No Drawings

PROCESS FOR PRODUCING M-XYLENE FROM O-XYLENE

This invention relates to a process for producing m-xylene, and particularly, to a process for producing m-xylene from o-xylene as a material by isomerization.

Xylene isomers consist of p-xylene, m-xylene, o-xylene and ethylbenzene. p-Xylene is industrially important as a material for polyester fibers or films; m-xylene, as a material for thermally stable aramid fibers or alkyd resins; o-xylene, as a material for plasticizers; and ethylbenzene, as a material for polystyrene. In particular, m-xylene has had an increasing demand in recent years as a material for thermally stable fibers such as poly(m-phenylene isophthalamide) fibers the production of which goes through a step of converting m-xylene into isophthaloyl chloride and a subsequent step of polycondensing isophthaloyl chloride with m-phenylenediamine.

Industrially, m-xylene is produced by the Mitsubishi Gas Chemical (MGC) xylene process which comprises contacting mixed xylenes with $HF-BF_3$ in the liquid phase to form selectively a complex of m-xylene with $HF-BF_3$, and separating it.

The MGC xylene process is excellent in that m-xylene can be selectively extracted from a mixed xylene material by complex formation and the reaction can be carried out at low temperatures and pressures in a compact reaction apparatus. However, it is defective in various respects. For example, $HF-BF_3$ used in the extraction step and the isomerization step is very corrosive on the reaction apparatus. Since the reaction is a homogeneous reaction in the liquid phase, a separate step of recovering the catalyst is required, and this adds to the cost of equipment. When an ordinary mixed xylene material is used, a step of rectification is required for separation of ethylbenzene. When p- and o-xylenes are not prepared as commercial products, they are recycled to the isomerization step. Hence, the amount of p- and o-xylenes to be fed to the isomerization step increases greatly, and an enormous amount of energy is consumed.

On the other hand, mixed xylenes ($C_8$ fraction) obtained from reformed or cracked gasoline contain m-xylene in a proportion close to a thermodynamically equivalent proportion. It is extremely difficult, however, to separate m-xylene industrially from these starting materials by a distillation or crystallization method because the xylene isomers have the following boiling points and melting points.

| Isomer | Boiling point (°C.) | Melting point (°C.) |
|---|---|---|
| o-xylene | 144.41 | −25.17 |
| m-xylene | 139.10 | −47.87 |
| p-xylene | 138.35 | +13.26 |
| ethylbenzene | 139.19 | −94.98 |

By distillation, o-xylene and ethylbenzene can be separated from the xylene isomers, but m-xylene or p-xylene cannot be individually separated from the xylene isomers. On the other hand, by cooling the m- and p-xylene mixture left after separation of o-xylene and ethylbenzene, p-xylene can be crystallized and recovered in a high concentration. It is impossible however to recover highly pure m-xylene from the remaining filtrate.

It is an object of this invention to provide a process for producing m-xylene from a hydrocarbon material containing o-xylene as a main ingredient.

Another object of this invention is to provide a process for producing m-xylene selectively by isomerization reaction from a hydrocarbon material containing o-xylene as a main ingredient.

Still another object of this invention is to provide a process for producing m-xylene selectively from a hydrocarbon material containing o-xylene as a main ingredient by isomerization reaction in the presence of a zeolite catalyst.

Yet another object of this invention is to provide a successive process for producing highly pure m-xylene from a hydrocarbon material containing o-xylene as a main ingredient.

A further object of this invention is to provide an industrial process for obtaining m-xylene from a hydrocarbon material containing o-xylene as a main ingredient.

Other objects of this invention along with its advantages will become apparent from the following description.

According to this invention, the objects and advantages of the invention are achieved by a process for producing m-xylene, which comprises isomerizing a hydrocarbon material containing o-xylene as a main ingredient in the presence of a catalyst composition comprising zeolite ZSM-4 and/or zeolite omega under such conditions that m-xylene is selectively formed, and recovering m-xylene by distillation from the resulting isomerization mixture containing o-xylene and m-xylene as main ingredients.

According to this invention, the use of zeolite ZSM-4 or zeolite omega enables o-xylene to be isomerized to m-xylene in a high conversion, and surprisingly, greatly inhibits secondary isomerization of the resulting m-xylene to p-xylene. Accordingly, by subjecting the resulting isomerization mixture to an ordinary distillation operation, highly pure m-xylene can be easily recovered as a distillate. A further industrial advantage of the invention is that no equipment for recovering the catalyst is required.

One characteristic feature of the present invention lies in the use of ZSM-4 or zeolite omega, a crystalline aluminosilicate zeolite. These zeolites are so-called low-silica zeolites having an $SiO_2/Al_2O_3$ mole ratio of from 3 to 20, and are structurally characterized in that they have a cage structure in addition to a channel system.

The zeolite ZSM-4 and zeolite omega are structurally similar to each other, and naturally occurring mazzite has a similar structure to these zeolites.

Zeolite ZSM-4 and zeolite omega used in the process of this invention are known per se. Zeolite ZSM-4 is described in British Pat. Nos. 1117568 and 1297256, and U.S. Pat. No. 4,021,447. Zeolite omega is described in British Pat. No. 1178186 (U.S. Pat. No. 4,241,036) and Journal of Chemical Society (A) 1470 (1970).

Zeolite ZSM-4 and zeolite omega have structures similar to each other. The similarities and differences between them are described in detail in Journal of Catalysis, 55, 240-249 (1978).

Zeolite ZSM-4 and zeolite omega are synthesized in the presence of, for example, sodium and tetramethyl ammonium ions. They are composed of gmelinite cages bound along the C-axis, and a channel system parallel to the C-axis has an opening diameter of 7.5 Å.

Zeolite ZSM-4 and zeolite omega used in this invention have a similar aluminosilicate structure. These zeolites are characterized by having X-ray diffraction data with strong peaks in the following interplanar spacings (d in Å).

| Characteristics of X-ray diffraction (points showing strong peaks) |
| --- |
| d (Å) |
| 9.10 ± 0.2 |
| 5.97 ± 0.07 |
| 3.80 ± 0.05 |
| 3.52 ± 0.05 |
| 3.16 ± 0.05 |
| 2.92 ± 0.05 |

Detailed X-ray diffraction data of zeolite ZSM-4 and zeolite omega used in this invention are shown below.

| ZSM-4 (see British Patent 1,297,256) | |
| --- | --- |
| Interplanar spacing d (Å) | Relative intensity |
| 9.1 ± 0.2 | vs |
| 7.94 ± 0.1 | mw |
| 6.90 ± 0.1 | m |
| 5.97 ± 0.07 | s |
| 5.50 ± 0.05 | mw |
| 5.27 ± 0.05 | mw |
| 4.71 ± 0.05 | mw |
| 4.39 ± 0.05 | w |
| 3.96 ± 0.05 | w |
| 3.80 ± 0.05 | s |
| 3.71 ± 0.05 | m |
| 3.63 ± 0.05 | m |
| 3.52 ± 0.05 | s |
| 3.44 ± 0.05 | m |
| 3.16 ± 0.05 | s |
| 3.09 ± 0.05 | m |
| 3.04 ± 0.05 | m |
| 2.98 ± 0.05 | m |
| 2.92 ± 0.05 | s |

The relative intensities are given in terms of the vs=very strong, s=strong, m=medium, w=weak and mw=medium weak.

| Zeolite omega (see British Patent 1,178,186) | |
| --- | --- |
| d (Å) | Relative intensity |
| 15.8 ± 0.4 | m |
| 9.1 ± 0.2 | vs |
| 7.9 ± 0.2 | m |
| 6.9 ± 0.2 | m |
| 5.95 ± 0.1 | m |
| 4.69 ± 0.1 | m |
| 3.79 ± 0.1 | s |
| 3.62 ± 0.05 | m |
| 3.15 ± 0.05 | m-s |
| 3.14 ± 0.05 | ms |
| 3.08 ± 0.05 | m |
| 3.03 ± 0.05 | m |
| 2.92 ± 0.05 | ms |

Zeolite ZSM-4 used in this invention, in the as-synthesized form, can be expressed by the chemical composition $$0.9 \pm 0.2 M_{2/n}O : Al_2O_3 : 3-20 SiO_2 : 0-20 H_2O$$

in which M is a cation, preferably an alkali metal cation (such as a sodium cation) and/or a nitrogen-containing cation such as a tetramethylammonium, choline salt or pyrrolidine cation, and n represents the valency of M.

Zeolite omega, in the as-synthesized form, can be expressed by the chemical composition $$[x(Me_4N)O + yNa_2O] : Al_2O_3 : 5-12 SiO_2 : 0-10 H_2O$$

in which Me represents methyl, x is 0 to 0.7, y is 0.5 to 1.5 and (x+y) is 0.5 to 1.5.

The above chemical composition of zeolite ZSM-4 and zeolite omega are in the as-synthesized form. In actual use as an isomerization catalyst in this invention, the above cations may be exchanged with other cations.

It should be understood that any species of zeolite ZSM-4 and zeolite omega which have the above X-ray diffraction characteristics and the above chemical compositions may be used in this invention. Preferably, to increase the activity of zeolite ZSM-4 and zeolite omega as a catalyst, cation sites derived from $AlO_2^-$, the constituent element, may be replaced by protons ($H^+$) This may be carried out by a known method comprising contacting the zeolite as synthesized with a proton supply source such as an aqueous solution of a mineral acid (e.g., hydrochloric acid or nitric acid), or an ammonium cation supply source such as ammonium chloride or aqueous ammonia, and drying and calcining it to eliminate ammonia and generate a proton in the cation site. In the process of this invention, the ratio of protons occupying cation sites of the crystalline aluminosilicate zeolite greatly affect the degree of the isomerization of o-xylene. Desirably, the proton occupying ratio based on the cation sites is at least 70%, preferably at least 90%. The remaining cation sites are occupied by an alkali metal ion, an alkaline earth metal ion, a transition metal ion and a lanthanide metal ion. These ions include those derived from materials for synthesizing zeolites, or those introduced as a result of ion exchange carried out after synthesis by using compounds containing these ions.

Another characteristic feature of the process of this invention is that the objects of the invention can be achieved by contacting a hydrocarbon material containing o-xylene as a main ingredient with the catalyst at a temperature of 50° to 250° C., which is much lower than the reaction temperatures used in the conventional isomerization of xylenes. It is known that a metal halide, for example a Lewis acid such as aluminum chloride has catalytic activity on the isomerization of xylenes at low temperature of, for example, room temperature. However, such a catalyst is troublesome to recover, and since its acid strength is high, the consecutive isomerization cannot sufficiently be suppressed. On the other hand, crystalline aluminosilicate zeolites have frequently been used as isomerization catalysts for the production of p-xylene, and examples of their use are described in detail, for example, in "Advance in Petroleum Chemistry and Refining", vol. 4, page 433 and U.S. Pat. Nos. 3,856,872, 3,856,873, 4,312,790, 4,385,195 and 4,224,141. The isomerization reaction temperature used in the production of p-xylene in the presence of such crystalline aluminosilicate zeolites is usually 250° to 550° C. No crystalline aluminosilicate zeolite has yet been discovered which permits sufficient proceeding of an isomerization of xylenes at lower temperatures.

The present invention is based on the discovery that zeolite ZSM-4 and zeolite omega show marked isomerization activity on o-xylene at temperatures lower than 250° C., and surprisingly ZSM-4 and omega enable this reaction to proceed even at temperatures below 200° C. while at the same time inhibiting consecutive isomerization reactions.

It is o-xylene which is to be isomerized in this invention. The starting material, therefore, is a hydrocarbon material containing o-xylene as a main ingredient. Desirably, the o-xylene content of the hydrocarbon material is at least 80% by weight, preferably at least 90% by weight. o-Xylene having a relatively high purity is easily available commercially, and high-purity o-xylene itself can also be used as the starting material in this invention. It is also possible however to recover the desired m-xylene from the isomerization reaction mixture by distillation, and use the remainder again as the starting material in the process of this invention. This material to be recycled contains not only the unreacted o-xylene but also m-xylene, p-xylene, $C_7$ aromatic hydrocarbons and $C_9$ aromatic hydrocarbons.

Thus, the starting material for the isomerization used in this invention may contain not more than 20% by weight, preferably not more than 10% by weight, of hydrocarbons other than o-xylene. The other hydrocarbons may be those originally contained in the starting material containing o-xylene or those resulting from the isomerization, and are, for example, $C_8$ aromatic hydrocarbons (m-xylene, p-xylene, ethylbenzene), benzene, toluene, trimethylbenzenes, ethyltoluenes and diethylbenzenes. Preferably, the amount of the other hydrocarbons is as small as possible in order to obtain highly pure m-xylene and reduce the burden in the step of separating m-xylene.

The preferred temperature used to carry out the isomerization in the process of this invention is 50° to 250° C. To achieve the objects of the invention fully, temperatures in the range of 100° to 200° C. are especially preferred. If the reaction temperature is lower than the specified limit, the conversion of the starting o-xylene is reduced. On the other hand, if the reaction temperature is higher than the specified upper limit, the conversion of o-xylene increases but the resulting m-xylene is converted to p-xylene (so-called consecutive isomerization reaction). Consequently, the concentration of p-xylene in the resulting product increases and the objects of this invention cannot be achieved.

Contacting of the hydrocarbon material with the zeolite-containing catalyst composition in the process of the invention may be carried out in the vapor phase or the liquid phase.

When the isomerization reaction is carried out in the vapor phase, the contacting of the hydrocarbon material with the zeolite-containing catalyst composition may be carried out so that the weight hourly space velocity [WHSV; the amount (g) of o-xylene fed per unit weight (g) of zeolite and per unit time (hour)] becomes 0.01 to 10, preferably 0.1 to 1. If WHSV is lower than 0.01, a large amount of the catalyst is required. If it is higher than 1, no sufficient conversion of o-xylene can be obtained, and the process is industrially disadvantageous. This vapor-phase isomerizaztion reaction may be carried out in a hydrogen stream. The amount of hydrogen to be supplied, in terms of the hydrogen-/oxylene mole ratio, is from 0.1 to 10, preferably from 0.5 to 5.

When the isomerization reaction is carried out in the liquid phase, a continuous or batchwise method may be used. If the reaction temperature is above the boiling point of o-xylene, it is necessary to pressurize the reaction system with an inert gas. Examples of the inert gas is hydrogen, helium, nitrogen or argon. The reaction pressure depends upon the reaction temperature, and the lowest pressure which can maintain the reaction system liquid suffices. Usually, it is atmospheric pressure to about 20 kg/cm$^2$-G, preferably about 2 to about 10 kg/cm$^2$-G.

In the continuous method, the liquid-phase isomerization may be carried out at a WHSV of 0.01 to 10, preferably 0.1 to 1. In the batchwise method, the amount of the catalyst used is 0.1 to 50% by weight, preferably 1 to 25% by weight.

Irrespective of the mode of the reaction in the process of this invention, the zeolite-containing catalyst composition used may be in the form of a powder, or a molded article such as pellets or tablets. In the case of the molded article, the proportion of zeolite in it is advantageously 1 to 100% by weight, preferably 10 to 90% by weight. To mold the zeolite, a refractory inorganic oxide is used as a binder generally used for zeolites. Examples of the refractory inorganic oxide are silica, alumina, silica-alumina, silica-magnesia, and kaolin. Alumina is especially preferred.

The reaction mixture obtained by the isomerization in accordance with this invention contain low-boiling aromatic hydrocarbons such as benzene and toluene, the unreacted o-xylene, m-xylene formed as a result of the isomerization reaction, and some amounts of high boiling aromatic hydrocarbons such as p-xylene and trimethylbenzenes. m-Xylene may be obtained from the reaction mixture by separating the low boiling fractions by distillation, and further distilling the remainder. Usually, the overhead effluent contains at least 90% of m-xylene, and o-xylene and the high boiling fractions which are the distillation bottoms are sent to the subsequent distillation step. The fraction containing at least 90% of m-xylene may be used as a final product, but as desired, may further be purified. The purification may preferably be effected by adsorptive purification method utilizing zeolite.

Specifically, the purification may be advantageously carried out by contacting the fraction containing at least 90% of m-xylene separated as above with a zeolite adsorbent to adsorb p-xylene in it and the p-xylene so adsorbed are removed.

Zeolite adsorbents are preferably those which permit selective adsorption of the by-product p-xylene. Zeolites having a p-xylenelene/m-xylene adsorptive separation factor of at least 1.1, preferably at least 2, are used. Adsorbents obtained by ion exchange of known Y-type, L-type, beta and ZSM-5 zeolites with various cations are advantageously used in view of their adsorption selectivity and adsorption capacity. Typical examples are described, for example, in U.S. Pat. Nos. 3,558,730, 3,558,732, 3,626,020, 3,663,638 and 3,793,385, and Japanese Patent Publication No. 29300/1977.

The use of the zeolite adsorbent exemplified above permits selective adsorption of p-xylene contained in the fraction containing at least 90% of m-xylene obtained by the isomerization reaction. After selective removal of p-xylene using the zeolite adsorbent, m-xylene having a purity of at least 95%, preferably at least 99%, can be easily obtained from the remaining liquid. The advantage that highly pure m-xylene is obtained by adsorbing and removing p-xylene using the zeolite adsorbent is due to the specificity of the isomerization in accordance with this invention. Since the isomerization reaction by this invention produces m- xylene selectively, the formation of p-xylene is much inhibited, A fraction obtained by removing the unreacted o-xylene and the low and high boiling components from the isomerization reaction mixture by distillation contains at least 90% of m-xylene. Thus, to adsorb and remove a minor porportion of p-xylene in such a reaction is very efficient.

Accordingly, the present invention offers an industrially advantageous and economical process by which highly pure m-xylene is obtained from o-xylene by a combination of the isomerization and zeolite adsorption.

As stated above, m-xylene of a high purity can be selectively produced in a high yield by the process of this invention. Furthermore, according to this process, the energy cost and the cost of facilities are very low because the reaction conditions are very mild and the catalyst is not corrosive and requires no recovery step.

The process of this invention will be illustrated in detail by the following examples.

I. Preparation of a Zeolite Catalyst Composition (a) Synthesis of ZSM-4 ZSM-4 was synthesized in accordance with the method described in British Pat. No. 1,297,256. Specifically, 137 g of water glass ($SiO_2 = 36.7\%$ by weight, $Na_2O = 16.4\%$ by weight) as dissolved in 162 ml of water, and 7.9 g of sodium hydroxide was added to prepare a solution A.

Separately, 31.5 g of aluminum sulfate 18-hydrate was dissolved in 90 ml of water to prepare a solution B. Furthermore, 4 g of tetramethyl ammonium chloride was dissolved in 32 g of water to prepare a solution C. While the solution A was stirred, the solution B and then the solution C were added. The mixture was introduced into a 500 ml autoclave, and before the autoclave was sealed up, zeolite SK-40 (a product of Union Carbide Corporation) was added as seed crystals. The autoclave was sealed up, and the gel was stirred at room temperature and 40 rpm for 40 hours. The stirred gel was then maintained at 110° C. for 72 hours at a stirring speed of 40 rpm. The contents were then taken out, filtered, and washed with water. The washed product was dried at 90° C. for 16 hours. The amount of the product yielded was 43.6 g, and the product had a $SiO_2/Al_2O_3$ mole ratio of 6.5. It had the X-ray diffraction pattern shown below. Thus, the zeolite was determined to be zeolite ZSM-4.

| $2\theta$ | Interplanar spacing d (Å) | Relative intensity I/Io |
|---|---|---|
| 5.35 | 16.50 | 3 |
| 5.60 | 15.77 | 9 |
| 9.05 | 9.76 | 4 |
| 9.70 | 9.11 | 100 |
| 11.20 | 7.89 | 12 |
| 12.90 | 6.86 | 46 |
| 14.85 | 5.96 | 37 |
| 16.15 | 5.48 | 13 |
| 16.85 | 5.26 | 4 |
| 18.90 | 4.69 | 18 |

-continued

| $2\theta$ | Interplanar spacing d (Å) | Relative intensity I/Io |
|---|---|---|
| 20.35 | 4.36 | 7 |
| 22.55 | 3.94 | 12 |
| 23.45 | 3.79 | 49 |
| 24.00 | 3.70 | 25 |
| 24.60 | 3.62 | 19 |
| 25.35 | 3.51 | 46 |
| 26.00 | 3.42 | 15 |
| 28.30 | 3.15 | 37 |
| 28.95 | 3.08 | 21 |
| 29.45 | 3.03 | 18 |
| 29.70 | 3.01 | 4 |
| 30.00 | 2.98 | 11 |
| 30.65 | 2.91 | 44 |
| 33.80 | 2.65 | 8 |
| 34.15 | 2.62 | 7 |
| 35.55 | 2.52 | 4 |
| 37.90 | 2.37 | 4 |
| 39.60 | 2.27 | 4 |

(b) Preparation of H-type zeolite

Fifty grams of each of ZSM-4 obtained in section (a) above and zeolite omega (ELZ-Q) obtained from Union Carbide Corporation, U.S.A. was immersed in 500 ml of a 10% aqueous solution of ammonium chloride, and then left to stand for one day under reflux to perform ion-exchange. This operation was repeated twice, and the product was separated, washed with water and dried overnight at 100° C. After the ion-exchange, these zeolites had a sodium content of less than 0.1% by weight.

The conversion to H-type zeolite was achieved by maintaining the resulting powder at 500° C. for 16 hours in an air stream in an electrical furnace to decompose the $NH_4^+$ ion into an ammonia gas.

(c) Molding of the catalyst composition

To each of the ZSM-4 and omega H-type zeolite powders prepared in (b) above was added an equal weight of alumina gel (300 mesh). They were fully mixed and molded into a size of 10 to 20 mesh.

The molded product was calcined in an electrical furnace at 500° C. in an air stream for 8 hours.

II Isomerization Reaction

Examples 1-2 and Comparative Examples 1-4

Five grams of the molded article obtained as above was filled in an atmospheric pressure fixed bed reactor. Under the reaction conditions described in Table 1, o-xylene and hydrogen were supplied. The composition of the product obtained in 1 to 2 hours after supplying the materials is shown in Table 1. For comparison, the same test was carried out on H-type mordenite (a product of Shokubai Kasei K. K.) and Ferrierite (Toso Co., Ltd.).

The results are also shown in Table 1.

The results given in Table 1 show that zeolites used in the process of this invention have high activity on the isomerization of o-xylene and give highly pure m-xylene.

TABLE 1

| Run | Example 1 | Example 2 | Comparative Example 1 | Comparative Example 2 | Comparative Example 3 | Comparative Example 4 |
|---|---|---|---|---|---|---|
| Zeolite | ZSM-4 | Omega | Mordenite | Ferrierite | Mordenite | Ferrierite |
| Reaction conditions | | | | | | |
| Temperature (°C.) | 170 | 180 | 180 | 180 | 260 | 260 |
| WHSV ($hr^{-1}$) | 2.0 | 2.0 | 2.0 | 2.0 | 2.0 | 2.0 |
| $H_2$/HC (mole ratio) | 1.0 | 1.0 | 1.0 | 1.0 | 1.0 | 1.0 |

TABLE 1-continued

| Run | Example 1 | Example 2 | Comparative Example 1 | Comparative Example 2 | Comparative Example 3 | Comparative Example 4 |
|---|---|---|---|---|---|---|
| Composition of the product (wt. %) | | | | | | |
| Low-boiling aromatics | 1.41 | 2.00 | 0.17 | 0.13 | 1.25 | 0.50 |
| p-Xylene | 1.52 | 1.33 | 0.52 | 0.64 | 5.11 | 3.65 |
| m-Xylene | 16.69 | 19.67 | 3.07 | 3.78 | 23.29 | 17.34 |
| o-Xylene | 78.34 | 74.64 | 96.00 | 95.28 | 68.70 | 77.80 |
| High-boiling aromatics | 2.04 | 2.43 | 0.23 | 0.17 | 1.65 | 0.70 |
| o-X conversion (%) | 21.7 | 25.4 | 4.0 | 4.7 | 31.3 | 22.2 |
| Xylene loss (%) | 3.3 | 4.4 | 0.4 | 0.3 | 2.9 | 1.2 |
| Purity of m-xylene (%) | 91.7 | 93.6 | 85.4 | 85.5 | 82.0 | 82.6 | o-X conversion = 100 − (concentration of o-xylene in the product)
Xylene loss = 100 − (concentration of xylenes in the product)

$$\text{Purity of m-xylene} = \frac{\left(\begin{array}{c}\text{Concentration of}\\\text{m-xylene in the product}\end{array}\right) \times 100}{\left(\begin{array}{c}\text{Concentration}\\\text{of m-xylene in}\\\text{the product}\end{array}\right) + \left(\begin{array}{c}\text{Concentration}\\\text{of p-xylene in}\\\text{the product}\end{array}\right)}$$

Example 3 and Comparative Example 5

Using zeolite ZSM-4 molded in (I) above, a performance test was carried out in the vapor phase. The reaction conditions and the results of the reaction obtained 1 to 2 hours after loading the o-xylene feed are summarized in Table 2.

TABLE 2

| Example | 3-(1) | 3-(2) | 3-(3) | Comparative Example 5-1 | Comparative Example 5-2 |
|---|---|---|---|---|---|
| Reaction conditions | | | | | |
| Temperature (°C.) | 150 | 170 | 190 | 270 | 320 |
| WHSV (hr$^{-1}$) | 0.5 | 1.0 | 2.0 | 2.5 | 5.0 |
| H$_2$/o-xylene (mole ratio) | 1.07 | 1.07 | 1.04 | 1.01 | 1.03 |
| Composition of the product (wt. %) | | | | | |
| Low-boiling aromatics | 2.56 | 3.31 | 1.06 | 9.73 | 3.71 |
| p-Xylene | 3.22 | 2.65 | 0.72 | 14.91 | 7.58 |
| m-Xylene | 28.85 | 23.81 | 8.58 | 41.99 | 31.81 |
| o-Xylene | 62.11 | 65.93 | 88.21 | 20.14 | 51.82 |
| High-boiling aromatics | 3.26 | 4.30 | 1.43 | 13.10 | 5.06 |
| o-X conversion (%) | 37.9 | 34.1 | 10.6 | 79.9 | 48.2 |
| Xylene loss (%) | 5.82 | 7.61 | 2.51 | 22.96 | 8.79 |
| Purity of m-xylene (%) | 90.0 | 90.0 | 92.3 | 73.8 | 80.8 |

The results given in Table 2 show that the ZSM-4 zeolite isomerization activity at very low temperatures below 250° C. in the isomerization reaction of o-xylene to m-xyleene in the vapor phase while the secondary isomerization to p-xylene was much inhibited.

EXAMPLE 4

In this example, the isomerization reaction of o-xylene to m-xylene was carried out in the liquid phase. Specifically, 100 g of o-xylene was charged into a stainless steel autoclave; and 10 g of H-type ZSM-4 zeolite powder synthesized in (I), (b) was introduced.

The reaction was carried out at 170° C. for 4 hours under autogenous pressure. The results are as follows:
o-xylene (OX) conversion: 46.4%
xylene loss: 4.5%
m-xylene purity: 89.9%
These results indicate that the process of this invention is excellent also in the liquid phase.

EXAMPLE 5

Thirty grams of o-xylene was taken into a 100 ml four-necked flask, and 10 g of H-type ZSM-4 zeolite powder obtained by calcination at 550° C. for 8 hours in an electrical furnace was fed into the flask. With stirring, the reaction was carried out at 110° C. The results obtained at the end of the reaction times indicated in Table 3 are summarized in Table 3.

TABLE 3

| Reaction time (hours) | 9 | 23 | 41 | 57 |
|---|---|---|---|---|
| Composition of the product (wt. %) | | | | |
| Low-boiling aromatics | 0.82 | 1.20 | 1.33 | 1.37 |
| p-Xylene | 0.98 | 1.58 | 2.13 | 2.48 |
| m-Xylene | 12.48 | 21.28 | 27.76 | 31.28 |
| o-Xylene | 84.46 | 74.17 | 66.70 | 62.58 |
| High-boiling aromatics | 1.26 | 1.75 | 2.07 | 2.27 |
| o-X conversion (%) | 15.5 | 25.8 | 33.3 | 37.4 |
| Xylene loss (%) | 2.08 | 2.97 | 3.42 | 3.66 |
| Purity of m-xylene (%) | 92.7 | 93.1 | 92.8 | 92.6 |

The results given in Table 3 show that the process of this invention can be carried out batchwise in the liquid phase under atmospheric pressure with much industrial advantage.

EXAMPLE 6

This example was carried out to show the stability with time of the process of this invention in the isomerization of o-xylene to m-xylene in the liquid phase continuous flow in a pressurized fixed bed reactor.

Ten grams of H-type ZSM-4 molded in (I), (c) was filled into the fixed bed reactor. The inside of the reactor was pressurized to 10 kg/cm$^2$-G with hydrogen, and the catalyst bed was maintained at 190° C. Then, o-xylene was fed at a rate of 10 g/hr. The composition of the product at the end of the times indicated in Table 4 is shown in Table 4.

TABLE 4

| Stream time (hours) | 56 | 174 | 258 | 544 |
|---|---|---|---|---|
| Composition of the product (wt. %) | | | | |
| Low-boiling aromatics | 0.20 | 0.15 | 0.09 | 0.09 |
| p-Xylene | 6.00 | 5.21 | 4.47 | 3.55 |
| m-Xylene | 51.14 | 45.35 | 40.52 | 36.22 |
| o-Xylene | 42.06 | 48.76 | 54.61 | 59.92 |
| High-boiling aromatics | 0.60 | 0.45 | 0.31 | 0.22 |
| o-X conversion (%) | 57.94 | 51.24 | 45.39 | 40.08 |
| Xylene loss (%) | 0.80 | 0.60 | 0.40 | 0.31 |
| Purity of m-xylene (%) | 89.50 | 89.70 | 90.07 | 91.07 |

The results given in Table 4 show that the process of this invention is advantageous in obtaining highly pure m-xylene continuously.

EXAMPLE 7

Commercial Y-type zeolite (a product of Shokubai Kasei K. K.) was converted to a potassium cation type (K-Y) by a known method using an aqueous solution of potassium chloride.

Zeolite ZSM (Na-ZSM-5) having a silica/alumina mole ratio of 32 was synthesized in accordance with the method described in U.S. Pat. No. 4526879. The two zeolites were each calcined at 500° C. for 8 hours in an electrical furnace, and an adsorption test for purification of m-xylene was conducted.

Specifically, 1 g of a feed (composed of 10% by weight of p-xylene and 90% by weight of m-xylene) and 20 ml of isooctane as a diluent were put in a 50 ml Erlenmeyer flask, and 5 g of each of the above zeolites was added, and the suspension was stirred overnight at room temperature. After determining the composition of the liquid phase, zeolite was separated by filtration and washed twice with 15 ml of n-hezane. The zeolite was again transferred into the Erlenmeyer flask, and 10 ml of water was added to desorb the adsorbed component. The suspension was stirred overnight at room temperature and the desorbed oil component was extracted with 10 ml of pentane and analyzed for the composition of the adsorption phase.

The results of the test are shown in Table 5. The results show that highly pure m-xylene can be obtained by adsorptive purification.

TABLE 5

|  |  | Zeolite | |
|---|---|---|---|
|  |  | K—Y | Na—ZSM—5 |
| Liquid | p-Xylene | 1.7 | 0 |
| phase (wt. %) | m-Xylene | 98.3 | 100.0 |
| Adsorption | p-Xylene | 10.8 | 52.9 |
| phase (wt. %) | m-Xylene | 89.2 | 47.1 |
| α PX/MX* |  | 7.0 | ∞ |

TABLE 5-continued

|  | Zeolite | |
|---|---|---|
|  | K—Y | Na—ZSM—5 |
| Amount adsorbed (cc/g) | 0.19 | 0.04 |

*Separation factor = $\dfrac{\text{[Concentration of p-xylene/concentration of m-xylene] adsorption phase}}{\text{[Concentration of p-xylene/concentration of m-xylene] liquid phase}}$

We claim:

1. A process for producing m-xylene, which comprises isomerizing a hydrocarbon material containing o-xylene as a main ingredient in the presence of a catalyst composition selected from the group consisting of zeolite ZSM-4, zeolite omega and mixtures thereof at a temperature of about 100° to 200° C. to selectively form m-xylene, and recovering m-xylene by distillation from the resulting isomerization mixture containing o-xylene and m-xylene as main ingredients.

2. The process of claim 1 in which the catalyst composition contains the hydrogen form of zeolite ZSM-4.

3. The process of claim 1 in which the catalyst composition contains the hydrogen form of zeolite omega.

4. The process of claim 1 in which the isomerization is carried out in the vapor phase.

5. The process of claim 4 in which the isomerization reaction is carried out under a pressure of about 10 mmHg to 10 kg/m$^2$-G.

6. The process of claim 1 in which the isomerization is carried out in the liquid phase.

7. The process of claim 6 in which the isomerization is carried out under a pressure ranging from atmospheric pressure to about 20 kg/mm$^2$-G.

8. The process of claim 1 in which the isomeriztion is carried out in the presence of hydrogen.

9. The process of claim 1 in which a fraction containing m-xylene as a main ingredient is recovered from the isomerization reaction mixture by distillation, and then this fraction is brought into contact with a zeolite adsorbent having a p-xylene/m-xylene adsorption ratio of at least 1.1 to obtain pure m-xylene as a raffinate.

10. The process of claim 9 in which the zeolite adsorbent is zeolite Y, zeolite L or zeolite ZSM-5.

* * * * *